United States Patent [19]
Bryant et al.

[11] Patent Number: 5,959,103
[45] Date of Patent: Sep. 28, 1999

[54] NAPHTHOFLUORENE COMPOUNDS, INTERMEDIATES, COMPOSITIONS, AND METHODS

[75] Inventors: Henry Uhlman Bryant; Jeffrey Alan Dodge, both of Indianapolis; Charles Willis Lugar, III, McCordsville, all of Ind.

[73] Assignee: Eli Lilly and Company, Indianapolis, Ind.

[21] Appl. No.: 09/163,424

[22] Filed: Sep. 30, 1998

Related U.S. Application Data

[62] Division of application No. 08/934,988, Sep. 22, 1997.
[60] Provisional application No. 60/026,715, Sep. 26, 1996.
[51] Int. Cl.[6] .................... C07D 295/08; C07D 207/06
[52] U.S. Cl. .................. 540/609; 544/173; 544/177; 546/205; 546/206; 548/576; 564/354
[58] Field of Search .................. 540/609; 544/173, 544/177; 546/205, 206; 548/576; 564/347, 353, 354

[56] References Cited

U.S. PATENT DOCUMENTS

| | | | |
|---|---|---|---|
| 3,274,213 | 9/1966 | Lednicer et al. | 260/326.5 |
| 3,394,125 | 7/1968 | Crenshaw | 260/326.5 |
| 3,413,305 | 11/1968 | Crenshaw | 260/326.5 |
| 3,974,186 | 8/1976 | Fleming et al. | 260/380 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,147,880 | 9/1992 | Jones et al. | 514/650 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,795 | 1/1996 | Bryant et al. | 514/212 |

FOREIGN PATENT DOCUMENTS

| | | |
|---|---|---|
| 0 065 962 | 1/1982 | European Pat. Off. . |
| 062 503 | 10/1982 | European Pat. Off. . |
| 0 729 951 | 9/1996 | European Pat. Off. . |
| 564 513 | 6/1975 | Switzerland . |
| 2 271 112 | 4/1994 | United Kingdom . |
| 2 303 628 | 2/1997 | United Kingdom . |
| WO 89/02893 | 4/1989 | WIPO . |
| WO 95/10513 | 4/1995 | WIPO . |
| WO 97 04763 | 2/1997 | WIPO . |

OTHER PUBLICATIONS

Crenshaw, R.R., et al., *J. Med. Chem.* 14 (12) :1185–1190 (1971).
Jones, C.D., et al., *J. Med. Chem.* 27 : 1057–1066 (1984).
Jones, C.D., et al., *J. Med. Chem.* 35: 931–938 (1992).

*Primary Examiner*—Richard L. Raymond
*Assistant Examiner*—Deepak R. Rao
*Attorney, Agent, or Firm*—Gilbert T. Voy

[57] ABSTRACT

The invention provides naphthofluorene compounds, intermediates, formulations, processes, and methods of inhibiting bone loss or bone resorption, particularly osteoporosis, cardiovascular-related pathological conditions, including hyperlipidemia, and estrogen-dependent cancer.

1 Claim, No Drawings

NAPHTHOFLUORENE COMPOUNDS, INTERMEDIATES, COMPOSITIONS, AND METHODS

This application is a divisional of application Ser. No. 08/934,988, filed Sep. 22, 1997 which claims the benefit of U.S. provisional application No. 60/026,715 filed Sep. 26, 1996.

BACKGROUND OF THE INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients.

Additionally, although osteoporosis is generally not thought of as a life threatening condition, a 20% to 30%. mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Estrogen dependent cancers are major diseases effecting both women and to a lesser extent men. Cancer cells of this type are dependent on a source of estrogen to maintain the orginal tumor as well as to proliferate and metastasize to other locations. The most common forms of estrogen dependent cancer are breast and uterine carcinomas. Current chemotherapy of these diseases relies primarily on the use of anti-estrogens, predominately tamoxifen. The use of tamoxifen, although efficaceous, is not without undesirable side-effects, for example, estrogen agonist properties, such as uterine hypertrophy and carcinogenic potential. Compounds of the current invention while showing the same or better potential for anti-cancer activity, also demonstrate a lower-potential for estrogen agonist activity.

In response to the clear need for new pharmaceutical agents which are capable of alleviating the symptoms of, inter alia, postmenopausal syndrome, the instant invention provides novel naphthofluorene compounds, pharmaceutical formulations thereof, and methods of using such compounds for the treatment of postmenopausal syndrome and other estrogen-related pathological conditions.

SUMMARY OF THE INVENTION

The instant invention relates to compounds of formula I:

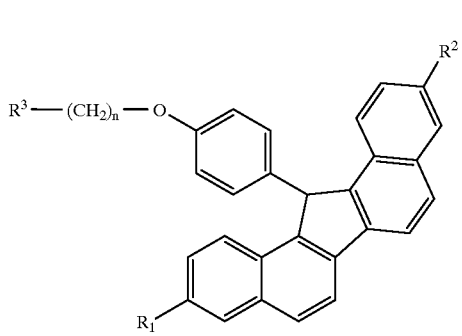

wherein:
$R^1$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —OSO$_2$($C_2$–$C_6$ alkyl);

$R^2$ is —H, —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —OSO$_2$($C_2$–$C_6$ alkyl);

$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and n is 2 or 3;

or a pharmaceutically acceptable salt or solvate thereof.

DETAILED DESCRIPTION OF THE INVENTION

In addition to providing compounds of formula I, the instant invention also relates to compounds of formula XI, which are useful as intermediates for the synthesis of compounds of formula I:

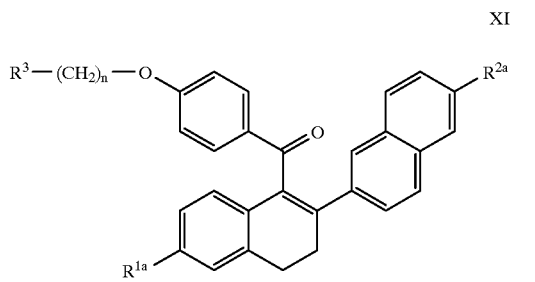

XI wherein:

$R^{1a}$ is —H or —OR$^5$, wherein $R^5$ is a hydroxy protecting group;

$R^{2a}$ is —H, —OR$^6$, wherein $R^6$ is a hydroxy protecting group, or halo; and $R^3$ and n are as previously defined.

The instant invention also relates to compounds of formula V, which are useful as intermediates for the synthesis of compounds of formula I:

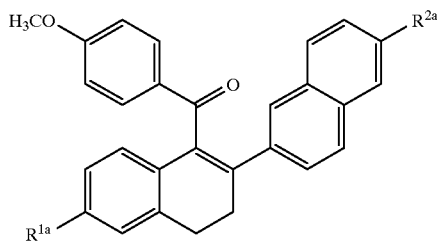

V wherein $R^{1a}$ and $R^{2a}$ are as previously defined.

The instant invention also relates to compounds of formula VI, which are useful as intermediates for the synthesis of compounds of formula I:

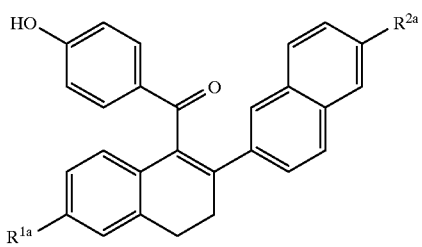

VI wherein $R^{1a}$ and $R^{2a}$ are as previously defined.

The instant invention also relates to compounds of formula VII, which are useful as intermediates for the synthesis of compounds of formula I:

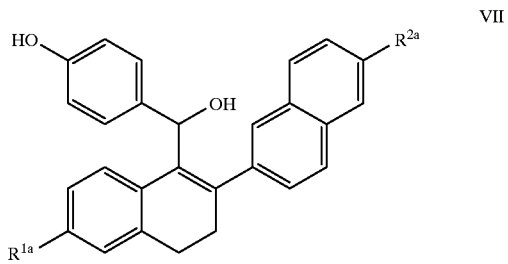

VII wherein $R^{1a}$ and $R^{2a}$ are as previously defined.

The instant invention also relates to compounds of formula II, which are useful as intermediates for the synthesis of compounds of formula I:

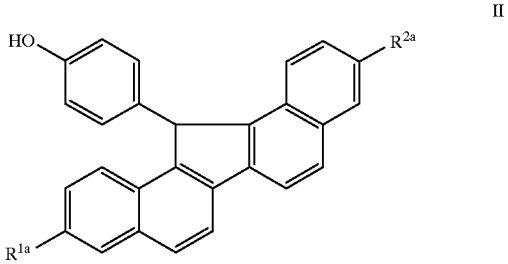

II wherein $R^{1a}$ and $R^{2a}$ are as previously defined.

The instant invention also relates to compounds of formula XII, which are useful as intermediates for the synthesis of compounds of formula I:

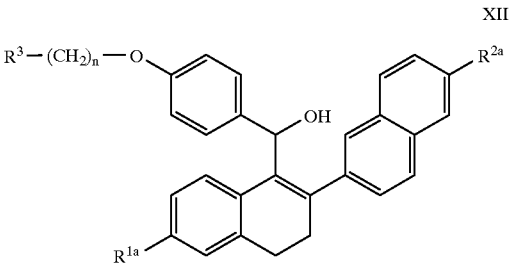

XII wherein $R^{1a}$, $R^{2a}$, $R^{3a}$, and n are as previously defined.

The instant invention further relates to pharmaceutical formulations containing compounds of formula I, and the use of said compounds at least for the inhibition of bone loss or bone resorption, particularly osteoporosis, cardiovascular-related pathological conditions, including hyperlipidemia, and estrogen-dependent cancer.

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is highly preferred.

The term "substituted phenyl" refers to a phenyl group having one or more substituents selected from the group consisting of $C_1$–$C_4$ alkyl, —$OC_1$–$C_4$ alkyl, hydroxy, nitro, chloro, fluoro, or tri(chloro or fluoro)methyl.

The term "hydroxy protecting group" contemplates numerous functionalities used in the literature to protect a hydroxyl function during a chemical sequence and which can be removed to yield the phenol. Included within this group would be acyls, mesylates, tosylates, benzyl, alkylsilyloxys, —$OC_1$–$C_4$ alkyls, and the like. Numerous reactions for the formation and removal of such protecting groups are described in a number of standard works including, for example, Protective Groups in Organic Chemistry, Plenum Press (London and New York, 1973); Green, T. W., Protective Groups in Organic Synthesis, Wiley, (New York, 1981); and The Peptides, Vol. I, Schrooder and Lubke, Academic Press (London and New York, 1965). Methods for removing preferred $R^7$ hydroxy protecting groups, particularly methyl and alkylsilyloxy, are essentially as described in the Examples, infra.

The term "leaving group" means a chemical entity which is capable of being displaced by an amino function via an $SN_2$ reaction. Such reactions are well known in the art and such groups would include halogens, mesylates, tosylates, and the like. A preferred leaving group would be bromo.

The term "solvate" represents an aggregate that comprises one or more molecules of the solute, such as a formula I compound, with one or more molecules of solvent.

The term "inhibit" includes its generally accepted meaning which includes prohibiting, preventing, restraining, and slowing, stopping, or reversing progression, severity, or ameliorating a resultant symptom or effect.

The compounds of the instant invention are named and numbered according to the Ring Index, The American Chemical Society, as follows:

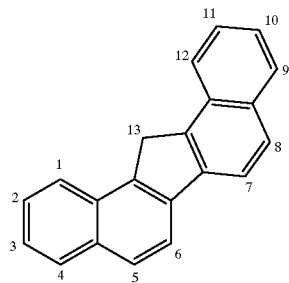

Compounds of formula I would include: 3-Hydroxy-13-[4-(2-piperidin-1-ylethoxy)phenyl]-13H-naphtho[a]fluorene, 3-Methoxy-13-[4-(2-piperidin-1-ylethoxy)phenyl]-13H-naphtho[a]fluorene, 3-Hydroxy-13-[4-(2-piperidin-1-ylethoxy)phenyl]-13H-10-hydroxynaphtho[a]fluorene, 3-Hydroxy-13-[4-(2-pyrrolidin-1-ylethoxy)phenyl]-13H-naphtho[a]fluorene, and the like.

The starting material for preparing compounds of the present invention is a compound of formula III

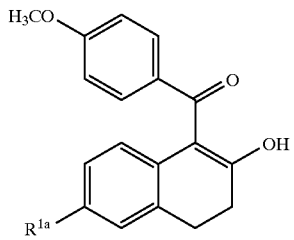

wherein $R^{1a}$ is —H or —$OR^5$ in which $R^5$ is a hydroxy protecting group.

Compounds of formula III are well known in the art and are prepared essentially as described by Jones et al. in U.S. Pat. No. 4,400,543 and Jones et al. in U.S. Pat. No. 5,147,880, and Bryant et al. U.S. Pat. No. 5,484,797, the disclosures of which are herein incorporated by reference. See also, Jones et al., J. Med. Chem., 35:931–8 (1992) and Jones et al., J. Med. Chem., 22:962 (1979).

In preparing compounds of the present invention, generally, a 1-acylated-2-tetralone of formula III is treated with a base to form its corresponding anion, which is reacted with diphenylchlorophosphate, providing an enol phosphate derivative of formula IV. The formula IV compound undergoes formal addition-elimination when treated with a naphthyl Grignard reagent, which results in substitution of the 2-phosphate substituent by the naphthyl moiety, thereby producing a compound of formula V. Dealkylation of a formula V compound by a thiolate anion demethylation reagent selectives dealkylates the group which is located para to the electron-withdrawing carbonyl group. The result of such selective dealkylation is a phenolic compound of formula VI, which can be reduced under the influence of hydride reducing agents to produce an allylic alcohol derivative of formula VII. The allylic alcohol is then cyclized under the influence of an acid catalyst to provide a naphthofluorene derivative of formula II. A compound of formula II serves as an intermediate to the compounds of this invention. This synthetic route is as shown below in Scheme I, and $R^{1a}$ and $R^{2a}$ are as defined above.

Scheme I

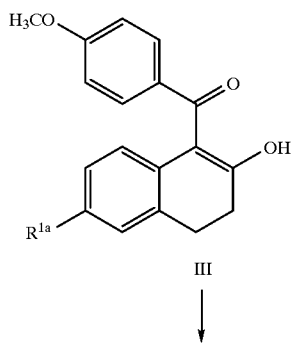

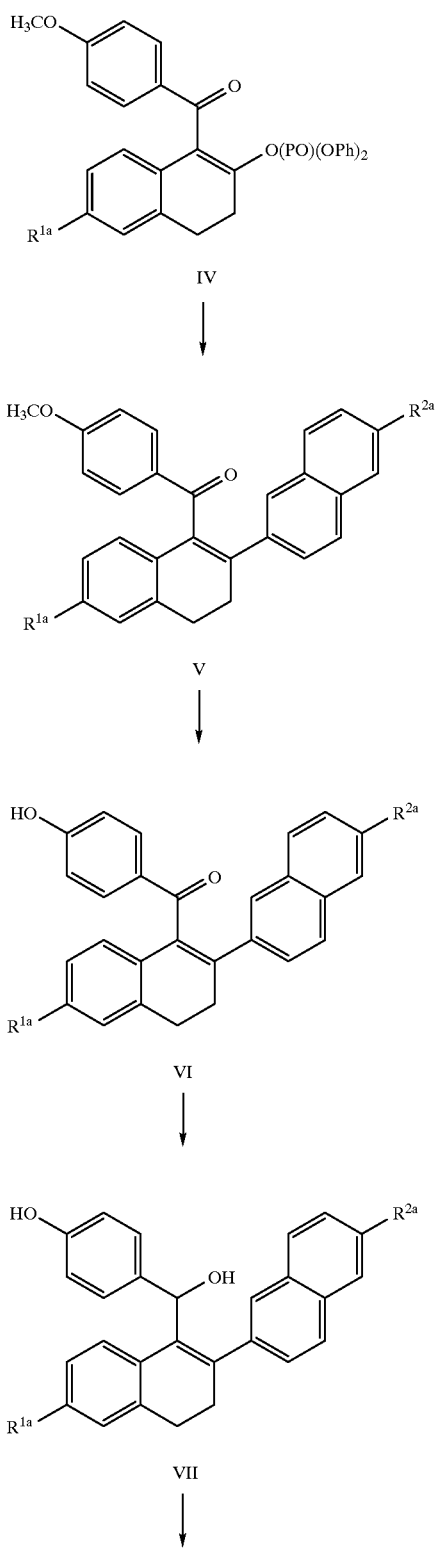

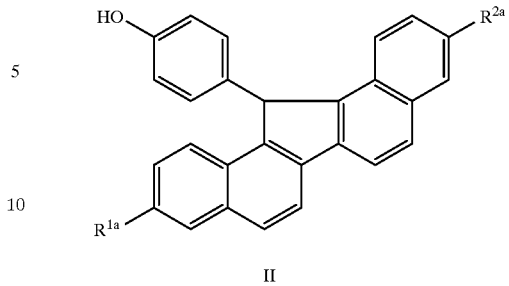

In the first step of the present process, a compound of formula III is converted to a dihydronaphthalene derivative of formula V via a two-step protocol, essentially as described by Jones et al., J. Med. Chem., 35:931–8 (1992). In essence, a formula III enolic compound is phosphorylated by one or more equivalents of a phosphorylating reagent which is a diarylchloro- or diarylbromo-phosphate and preferably diphenylchlorophosphate. This reaction may be carried out in a variety of inert solvents including ethers, THF, dioxane, ethyl acetate, toluene, and acetonitrile and in the presence of an acid scavenger such as an alkali metal hydride, alkali metal hydroxide, or alkali metal carbonate or a trialkyl amine such as triethyl amine. The alkali metal base or tertiary amine may also act as a basic catalyst in the phosphorylation process. Although it is preferable to run the reaction at ice bath temperature so as to avoid unwanted side products, elevated temperatures can also be used, but they are usually unnecessary to complete the phosphorylation reaction. The product of the phosphorylation reaction, an enol phosphate derivative of formula IV may be isolated by usual techniques, such as chromatography. However, it is most convenient to generate the enolphosphate using a solvent/ acid scavenger combination which is compatable with the next step of the reaction (addition of a Grignard reagent). Thus, the combination of sodium hydride in THF under a nitrogen atmosphere is preferred, and provides a rapid phosphorylation leading to a compound of formula IV.

The intermediate enol phosphate, either isolated or generated in situ, may then be reacted with one or more equivalents of a naphthyl Grignard reagent or a naphthyl lithium organocuprate reagent. One to two equivalents of a naphthyl magnesium bromide is preferred, and 4-methoxynaphthyl magnesium bromide is particularly preferred. The reaction is typically conducted at ice bath temperature to minimize side reactions, but elevated temperatures can be used to increase the rate of the reaction. The addition of the naphthyl moiety, followed by the elimination of the phosphate leaving group (formally an addition, elimination process) gives rise to a dihydronaphthalene derivative of formula V, which can be isolated by conventional techniques such as crystallization or chromatography.

The resulting dihydronaphthalene derivative of formula V is then demethylated to provide an intermediate of formula VI. In order to accomplish regioselective demethylation at the methoxy group para to the carbonyl, a nucleophilic demethylation reagent is used, and alkali metal thiolates (alkali metal salt of an organic thiol) are preferred. Especially preferred are lithium thioethylate or lithium thiomethylate, in excess to the extent of 1.2 or more equivalents of the demethylation reagent over the substrate. The reaction is conducted under an inert atmosphere to preserve the demethylation reagent and in a solvent which is practically inert to the nucleophilic nature of the thiolate reagent. Suitable solvents for the demethylation are those which are most conducive to bimolecular nucleophilic displacement reactions, and these include dimethylsulfoxide dimethylformamide, dimethylacetamide, and THF. Anhydrous dimethylformamide is preferred. In order to simultaneously achieve a satisfactory reaction rate and also obtain good control of the selectivity for demethylation at the site para to the carbonyl group, it is important to carefully control the temperature of the reaction. Although the demethylation process will take place in the range of temperatures from 60° C. to 120° C., it is advantageous to use a temperature in the range of 80°–90° C. to optimize the yield of the desired product. A temperature of 80° C. is particularly preferred. Under the preferred reaction conditions, the transformation from a formula V compound to a formula VI compound is complete after heating for about 2 to 4 hours at the indicated temperature.

A formula VI compound is added to an appropriate solvent and reacted with a reducing agent such as, for example, lithium aluminum hydride (LAH).

The amount of reducing agent used in this reaction is an amount sufficient to reduce the carbonyl group of formula VI to form the carbinol compounds of formula VII. Generally, a liberal excess of the reducing agent per equivalent of the substrate is used.

Appropriate solvents include any solvent or mixture of solvents which will remain inert under reducing conditions. Suitable solvents include diethyl ether, dioxane, and tetrahydrofuran (THF). The anhydrous form of these solvents is preferred, and anhydrous THF is especially preferred.

The temperature employed in this step is that which is sufficient to effect completion of the reduction reaction. Ambient temperature, in the range from about 17° C. to about 25° C., generally is adequate.

The length of time for this step is that amount necessary for the reaction to occur. Typically, this reaction takes from about 1 hour to about 20 hours. The optimal time can be determined by monitoring the progress of the reaction via conventional chromatographic techniques.

In the final transformation shown in Scheme I, the allylic alcohol derivative of formula VI undergoes a cyclization-dehydration process which produces the naphthofluorene derivative of formula II. This process is acid-catalyzed and a variety of mineral acids, Lewis acids, and organic acids stronger than acetic acid may be used. Among these catalysts are alkylsulfonic acids, aryl sulfonic acids, sulfuric acid, hydrochloric acid, hydrobromic acid, polyphosphoric acid, and boron trifluoride etherate. Hydrochloric acid is preferred. The cyclization reaction typically proceeds at room temperature, but higher temperatures may be advantageous in speeding up the reaction rate.

Under the preferred reaction conditions, the transformation from a formula VII compound to a formula II compound is complete after stirring for about 5 minutes to about 2 hours at 50° C. temperature or by stirring for overnight at ambient temperature.

Compounds of formula II are useful for the preparation of pharmaceutically active compounds of formula I of the present invention.

Upon preparation of a formula II compound, it is reacted with a compound of formula VIII $$R^3\text{—}(CH_2)_n\text{—}Q \qquad \text{VIII}$$

wherein $R^3$ and n are as defined above and Q is a bromo or, preferably, a chloro moiety, to form a compound of formula Ia. The formula Ia compound is then deprotected, when $R^5$ and/or $R^6$ hydroxy protecting groups are present, to form a compound of formula Ib. These process steps are shown in Scheme II below.

Scheme II

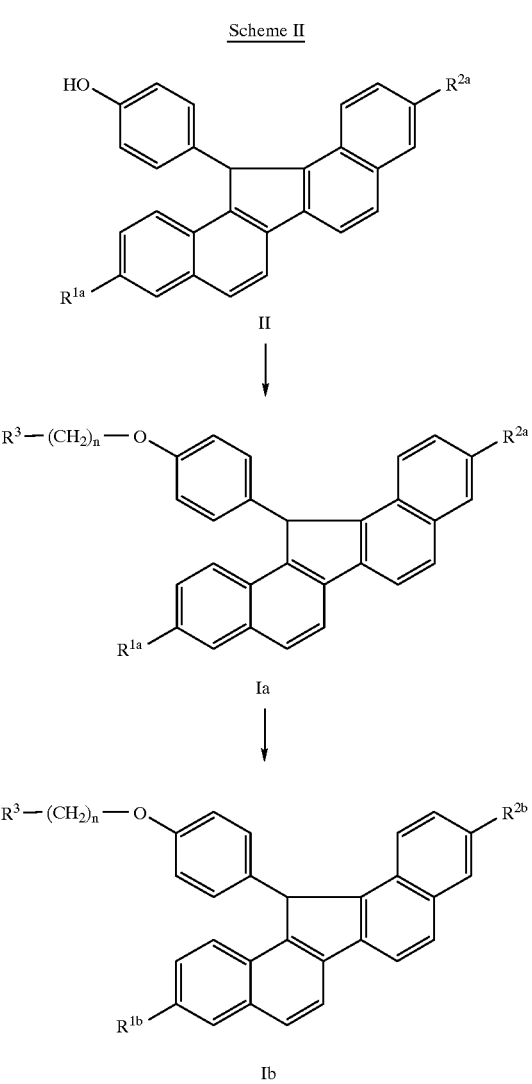

wherein:
$R^{1a}$, $R^{2a}$, $R^3$, and n are as defined above;
$R^{1b}$ is —H or —OH; and
$R^{2b}$ is —H, —OH, or halo;
or a pharmaceutically acceptable salt thereof.

In the first step of the process shown in Scheme II, the alkylation is carried out via standard procedures. Compounds of formula VIII are commercially available or are prepared by means well known to one of ordinary skill in the art. Preferably, the hydrochloride salt of a formula VIII compound, particularly 2-chloroethylpiperidine hydrochloride, is used.

Generally, at least about 1 equivalent of formula II substrate are reacted with 2 equivalents of a formula VIII compound in the presence of at least about 4 equivalents of an alkali metal carbonate, preferably cesium carbonate or potassium carbonate, and an appropriate solvent.

Solvents for this-reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Often, ambient temperature is sufficient and preferred, but in certain cases, higher temperatures may be required.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

As an alternative for preparing compounds of formula Ia, a formula II compound is reacted with an excess of an alkylating agent of the formula

$$Q-(CH_2)_n-Q'$$

wherein Q and Q' each are the same or different leaving group, in an alkali solution. Appropriate leaving groups include the sulfonates such as methanesulfonate, 4-bromobenzenesulfonate, toluenesulfonate, ethanesulfonate, isopropylsulfonate, 4-methoxybenzenesulfonate, 4-nitrobenzenesulfonate, 2-chlorobenzenesulfonate, triflate, and the like, halogens such as bromo, chloro, and iodo, and other related leaving groups. Halogens are preferred leaving groups and bromo is especially preferred.

A preferred alkali solution for this alkylation reaction contains potassium carbonate in an inert solvent such as, for example, methyethyl ketone (MEK) or DMF. In this solution, the 4-hydroxy group of the phenolic moiety of a formula II compound exists as a phenoxide ion which displaces one of the leaving groups of the alkylating agent.

This reaction is best when the alkali solution containing the reactants and reagents is brought to reflux and allowed to run to completion. When using MEK as the preferred solvent, reaction times run from about 6 hours to about.20 hours.

The reaction product from this step is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, or other secondary amines, via standard techniques, to form compounds of formula Ia. Preferably, the hydrochloride salt of piperidine is reacted with the alkylated compound of formula IIb in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step can be monitored via standard chromatographic techniques.

An alternative route for preparing compounds of the present invention is as depicted in Scheme III, in which $R^{1a}$, $R^{2a}$ and $R^3$ are as defined above.

Scheme III

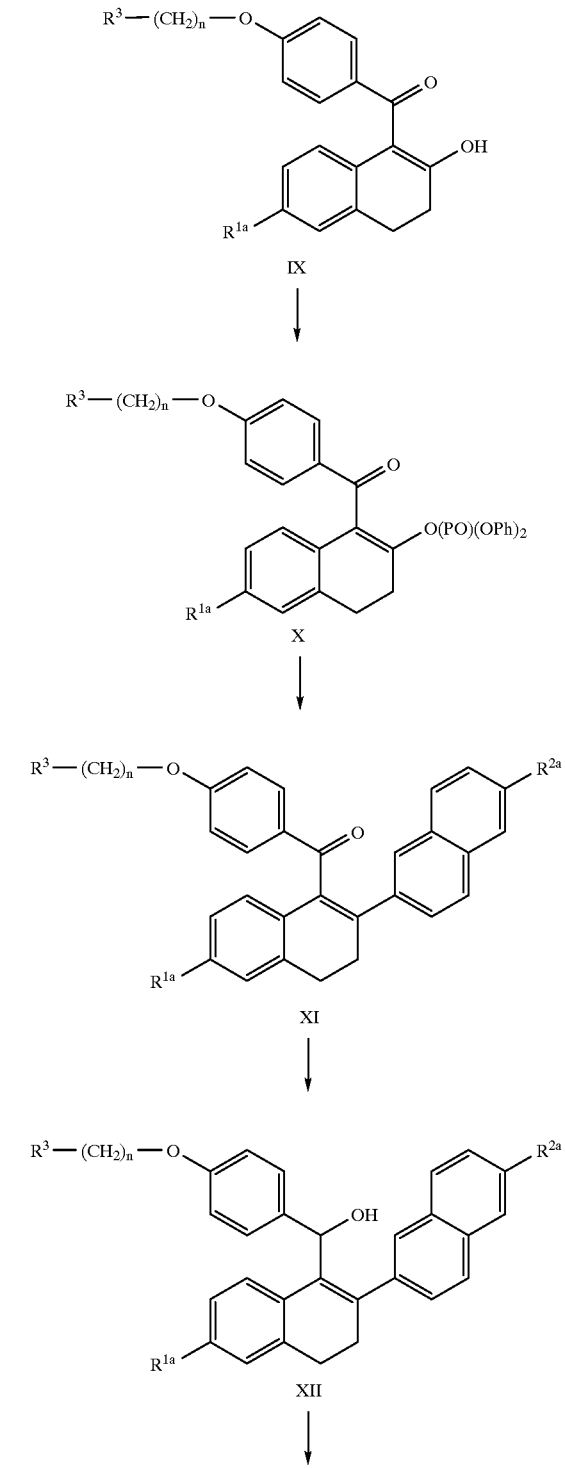

-continued

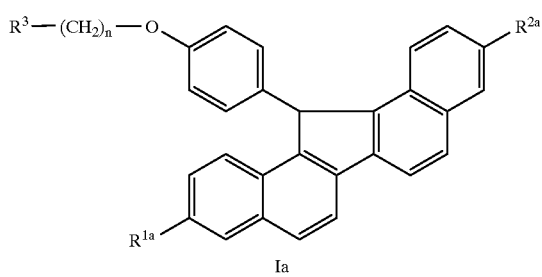

Ia

In this alternative, the starting material, a 1-acylated-2-tetralone of formula IX already includes the basic side chain moiety. The compound of formula IX treated with a base to form its corresponding anion, which is reacted with diphenylchlorophosphate, providing an enol phosphate derivative of formula X. The formula X compound undergoes formal addition-elimination when treated with a naphthyl Grignard reagent, which results in substitution of the 2-phosphate substituent by the naphthyl moiety, thereby producing a naphthalene compound of formula XI. Reduction of the carbonyl group to produce a benzylic alcohol of formula XII and subsequent cyclization under acidic conditions provides a formula Ia compound of this invention In essence, a formula IX enolic compound which already bears the basic side chain is phosphorylated by one or more equivalents of a phosphorylating reagent which is a diarylchloro- or diarylbromo-phosphate and preferably diphenylchlorophosphate. This reaction, may be carried out in a variety of inert solvents including ethers, THF, dioxane, ethyl acetate, toluene, and acetonitrile and in the presence of an acid scavenger such as an alkali metal hydride, alkali metal hydroxide, or alkali metal carbonate or a trialkyl amine such as triethyl amine. The alkali metal base or tertiary amine may also act as a basic catalyst in the phosphorylation process. Although it is preferable to run the reaction at ice bath temperature so as to avoid unwanted side products, elevated temperatures can also be used, but they are usually unnecessary to complete the phosphorylation reaction. The product of the phosphorylation reaction, an enol phosphate derivative of formula X may be isolated by usual techniques, such as chromatography. However, it is most convenient to generate the enolphosphate using a solvent/ acid scavenger combination which is compatable with the next step of the reaction (addition of a Grignard reagent). Thus, the combination of sodium hydride in THF under a nitrogen atmosphere is preferred, and leads to a rapid phosphorylation leading to a compound of formula X.

The intermediate enol phosphate of formula X is either isolated or generated in situ, and is then reacted with one or more equivalents of a naphthyl Grignard reagent or a naphthyl lithium organocuprate reagent. One to two equivalents of a naphthyl magnesium bromide is preferred, and naphthyl magnesium bromide or 4-methoxynaphthyl magnesium bromide is particularly preferred. The reaction is typically conducted at ice bath temperature to minimize side reactions, but elevated temperatures can be used to increase the rate of the reaction. The addition of the naphthyl moiety, followed by the elimination of the phosphate leaving group (formally an addition, elimination process) gives rise directly to a dihydronaphthalene derivative of formula XI, which can be isolated by conventional techniques such as crystallization of the free base or salts or chromatography of the former.

The reduction of the carbonyl group of a compound of formula XI to the carbinol of formula XII is effected in the same manner as provided above for Scheme II.

In the final transformation shown in Scheme III, the dihydronaphthalene derivative of formula XII undergoes a cyclization-dehydration process which produces the naphthofluorene derivative of formula Ia. This process is acid-catalyzed and a variety of mineral acids, Lewis acids, and organic acids may be used. Among these catalysts are alkylsulfonic acids, aryl sulfonic acids, sulfuric acid, hydrochloric acid, hydrobromic acid, polyphosphoric acid, and boron trifluoride etherate. Hydrochloric acid is preferred. The cyclization reaction typically proceeds at room temperature, but higher temperatures may be advantageous in speeding up the reaction rate.

Under the preferred reaction conditions, the transformation from a formula XII compound to a formula Ia compound is complete after stirring for about 5 minutes to about 2 hours at 50° C. temperature or by stirring for overnight at ambient temperature.

Compounds of formula Ia, in which $R^5$ and/or $R^6$, when present, are $C_1$–$C_4$ alkyl, preferably methyl, are pharmaceutically active for the methods herein described and are encompassed by the definition herein of compounds of formula I. Both isomers and mixtures of isomers generated at the 13-position are contemplated by, and within the scope of, the compounds of formula I.

Preferred compounds of formula I are obtained by cleaving, when present, the $R^5$ and $R^6$ hydroxy protecting groups of formula Ia compounds via well known procedures. Numerous reactions for the formation and removal of such protecting groups are described in a number of standard works including, for example, Protective Groups in Organic Chemistry, Plenum Press (London and New York, 1973); Green, T. W., Protective Groups in Organic Synthesis, Wiley, (New York, 1981); and The Peptides, Vol. I, Schrooder and Lubke, Academic Press (London and New York, 1965). Methods for removing preferred $R^5$ and/or $R^6$ hydroxy protecting groups, particularly methyl, are essentially as described in the Examples, infra.

Alternatively, compounds such as those represented by formula Ia are prepared from a compound of formual XI in a novel one-pot reaction in which a compound of formula XI is treated with a Lewis acid such as $AlCl_3$ and ethanethiol. This protocol causes cyclization to form the naphtho[a] fluorene as well as deprotecting the methyl ether group.

Other preferred compounds of formula I are prepared by replacing the 3-position and/or 10-position hydroxy moieties, when present, with a moiety of the formula —O—CO—($C_1$–$C_6$ alkyl), or —O—$SO_2$—($C_2$–$C_6$ alkyl) via well known procedures. See, for example, U.S. Pat. No. 4,358,593.

For example, when an —O—CO($C_1$–$C_6$ alkyl) group is desired, a mono- or dihydroxy compound of formula I is reacted with an acylating agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, for example, Haslam, et al., Tetrahedron, 36:2409–2433 (1980).

The present reactions are carried out at moderate temperatures, in the range from about −25° C. to about 100°

C., frequently under an inert atmosphere such as nitrogen gas. However, ambient temperature is usually adequate for the reaction to run.

Acylation of a 3-position and/or 10-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$ and/or $R^2$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, for example, Bull. Chem. Soc. Japan, 38:1979 (1965), and Chem. Ber., 788 and 2024 (1970).

Each of the above techniques which provide —O—CO— ($C_1$–$C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the 3-position and/or 10-position hydroxy group of a formula I compound is converted to a group of the formula —O—$SO_2$—($C_2$–$C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, J. Am. Chem. Soc., 97:2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting bone loss or bone resorption, particularly osteoporosis, and cardiovascular-related pathological conditions including hyperlipidemia, and related cardiovascular pathologies.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to inhibit the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, one to three times per day. Such dosages will be administered to a patient in need thereof usually at least for thirty days, and more typically for six months, or chronically.

The formulations which follow are given for purposes of illustration and are not intended to be limiting in any way. The total active ingredients in such formulations comprises from 0.1% It to 99.9% by weight of the formulation. The term "active ingredient" means a compound of formula I.

Formulation 1: Gelatin Capsules

| Ingredient | Quantity (mg/capsule) |
|---|---|
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
|---|---|
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50°–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
|---|---|
| Active Ingredient | 0.25 |
| Ethanol | 29.75 |
| Propellant 22 | 70.00 |
| (Chlorodifluoromethane) | |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
|---|---|
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension
Suspensions each containing 0.1–1000 mg of a compound of formula I per 5 mL dose.

| Ingredient | Weight |
|---|---|
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1

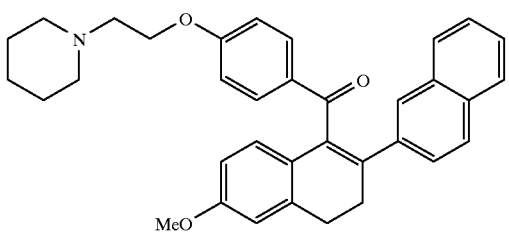

To a suspension of sodium hydride (0.90 g of a 60% oil dispersion, 22.42 mmol) stirring in THF (100 mL) at 0° C.

was added a mixture of dipheniylchlorophosphate (3.30 mL, 22.47 mmol) and the compound of formula III (8.3 g, 20.42 mmol) in THF (100 mL). After 2.5 h, the resulting solution was quenched with saturated aqueous ammonium chloride. The reaction mixture was diluted with ethyl acetate and extracted consecutively with saturated aqueous solutions of ammonium chloride, sodium hydroxide, and sodium chloride. The organic extracts were dried (sodium sulfate) and filtered. Concentration afforded a dark oil which was dissolved in THF (150 mL). This solution was cooled to −78° C. and naphthylmagnesium bromide solution (150 ml) (was made using the following procedure: To 3.0 g magnesium turnings in THF (150 ml) under nitrogen was added 2-bromonaphthylene (12.7 g, 61.27 mmol). The solution was allowed to exotherm to reflux, then stirred at room temperature for 4 hours. The resulting solution was decanted away from unreacted magnesium and used as is.) was added. After complete consumption of the enol phosphate intermediate, the reaction was warmed to −30° C. and quenched with saturated aqueous ammonium chloride. The mixture was then extracted with ethyl acetate and the combined organic extracts washed with saturated aqueous ammonium chloride, 1 N aqueous NaOH, and brine. The resulting dark oil was purified by flash chromatography (silica gel, chloroform to 5% methanol/chloroform gradient) to give 4.9 g (60%) of the crude desired product as a dark yellow oil: $^1$H NMR is consistant with structure. MS/FD—517.

EXAMPLE 1

3-Hydroxy-13-[4-(2-piperidin-1-ylethoxy)phenyl]-13H-naphtho[a]fluorene

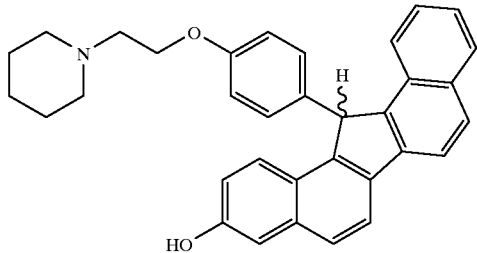

To a solution of a compound of Preparation 1 (4.5 g, 8.70 mmol) stirring in $CH_2Cl_2$ (200 mL) at room temperature was added ethanethiol (3.2 mL, 43.5 mmol) followed by $AlCl_3$ (5.80 g, 43.5 mmol). After stirring vigorously for 0.5 h, the dark red solution was quenched with saturated aqueous sodium bicarbonate. The resulting mixture was extracted with saturated aqueous sodium bicarbonate and brine. The organic extract was dried (sodium sulfate), filtered, and concentrated. The resulting dark oil was purified by flash chromatography (silica gel, 2% to 5% MeOH/CHCl$_3$ gradient) to give 1.6 g (40%) of the desired product as an orange foam: $^1$H NMR is consistant with structure. MS/FD—485.

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.70° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17$^\alpha$-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine:xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotemetrically at 500 nm. Cholesterol concentration was then calculated against a standard curve.

Uterine Eosinophil Peroxidase (EPO) Assay. Uteri were kept at 4° C. until time of enzymatic analysis. The uteri were then homogenized in 50 volumes of 50 mM Tris buffer (pH −8.0) containing 0.005% Triton X-100. Upon addition of 0.0% hydrogen peroxide and 10 mM 0-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17$^\alpha$-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17$^\alpha$-ethynyl estradiol (EE$_2$; an orally available form of estrogen), and rats treated with certain compounds of the instant invention. Although EE$_2$ caused a decrease in serum cholesterol when orally administered at 0.1 mg/kg/day, it also exerted a stimulatory action on the uterus so that EE$_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art. the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound | Dose mg/kg[a] | Uterine weight[b] (% increase vs. OVX) | Uterine EPO $(V_{max})$[c] | Serum Cholesterol[d] (% decrease vs. OVX) |
|---|---|---|---|---|
| $EE_2$[e] | 0.1 | 139.2 | 139.8 | 90.2 |
| Example 1 | 0.01 | 71.3 | 17.4 | 5 |
|  | 0.1 | 81.6 | 74.1 | 46.9 |
|  | 1.0 | 97.2 | 113.7 | 65.2 |
|  | 10.0 | 99.4 | 138.3 | 66.1 |

[a]mg/kg PO
[b]Uterine Weight % increase versus the ovariectomized controls
[c]Eosinophil peroxidase, $V_{max}$
[d]Serum cholesterol decrease versus ovariectomized controls
[e]17-$\alpha$-Ethynyl-estradiol
*p < .05

In addition to the demonstrated benefits of the compounds of the instant invention, the above data clearly demonstrate that compounds of formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals is also scanned by quantitative computed tomography.

In accordance with the above procedures, compounds of the instant invention and ethynyl estradiol ($EE_2$) in 20% hydroxypropyl $^\beta$-cyclodextrin are orally administered to test animals. Results are reported as percent protection relative to ovariectomy.

In summary, ovariectomy of the test animals will cause a significant reduction in femur density compared to intact, vehicle treated controls. Orally administered ethynyl estradiol ($EE_2$) prevented this loss, but the risk of uterine stimulation with this treatment is ever-present.

MCF-7 Proliferation Assay

MCF-7 breast adenocarcinoma cells (ATCC HTB 22) were maintained in MEM (minimal essential medium, phenol red-free, Sigma, St. Louis., Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 "/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium ($Ca^{++}/Mg^{++}$ free HESS (phenol red-free) supplemented with 10 mM HEPES and 2 mM EDTA). Cells were washed twice with assay medium and adjusted to 80,000 cells/mL. Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 50% $CO_2$ humidified incubator, microcultures were pulsed with tritiated thymidine (1 "Ci/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallace BetaPlace $\beta$ counter. Results obtained from this assay indicated a compound of Example 1 was a 4.5 nM inhibitor of MCF-7 breast cancer proliferation.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenzo[a]anthracene (DMBA). About 6 weeks after DMEA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

We claim:
1. A compound of formula XI:
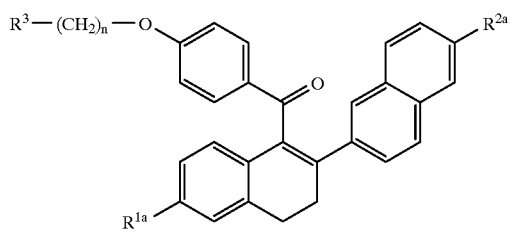
wherein:
$R^{1a}$ is —H or —$OR^5$, wherein $R^5$ is a hydroxy protecting group;
$R^{2a}$ is H, —$OR^6$, wherein $R^6$ is a hydroxy protecting group, or halo;
$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and
n is 2 or 3.
* * * * *